(12) United States Patent
De Castro et al.

(10) Patent No.: US 10,328,091 B2
(45) Date of Patent: Jun. 25, 2019

(54) COMPOSITION COMPRISING FUT2-DEPENDENT OLIGOSACCHARIDES AND LACTO-N-NEOTETRAOSE FOR USE IN PROMOTING BRAIN DEVELOPMENT AND COGNITION

(71) Applicant: NESTEC S.A., Vevey (CH)

(72) Inventors: Carlos Antonio De Castro, Geneva (CH); Norbert Sprenger, Savigny (CH); Sagar Thakkar, Brent (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/522,575

(22) PCT Filed: Oct. 29, 2015

(86) PCT No.: PCT/EP2015/075088
§ 371 (c)(1),
(2) Date: Apr. 27, 2017

(87) PCT Pub. No.: WO2016/066735
PCT Pub. Date: May 6, 2016

(65) Prior Publication Data
US 2017/0333462 A1    Nov. 23, 2017

(30) Foreign Application Priority Data

Oct. 31, 2014 (EP) .................................... 14191277

(51) Int. Cl.
*A61K 31/702* (2006.01)
*A23L 33/00* (2016.01)
*A23L 33/10* (2016.01)

(52) U.S. Cl.
CPC ............ *A61K 31/702* (2013.01); *A23L 33/10* (2016.08); *A23L 33/30* (2016.08); *A23L 33/40* (2016.08); *A23V 2002/00* (2013.01); *A23V 2250/284* (2013.01)

(58) Field of Classification Search
None
See application file for complete search history.

(56) References Cited

U.S. PATENT DOCUMENTS

| 8,711,674 | B2 * | 4/2014 | Gerakoulis | H04B 1/109 370/204 |
| 9,763,465 | B2 * | 9/2017 | Sprenger | A23L 33/40 |
| 9,854,826 | B2 * | 1/2018 | Sprenger | A23L 33/21 |
| 2012/0172319 | A1 | 7/2012 | Chow et al. | |
| 2012/0219526 | A1 | 8/2012 | Klassen et al. | |
| 2013/0243797 | A1 * | 9/2013 | Sprenger | A23L 33/21 424/184.1 |
| 2016/0287618 | A1 * | 10/2016 | Sprenger | A61K 45/06 |
| 2018/0036323 | A1 * | 2/2018 | Sprenger | A61K 31/702 |
| 2018/0042949 | A1 * | 2/2018 | Sprenger | A61K 31/702 |
| 2018/0078572 | A1 * | 3/2018 | Sprenger | A61K 31/702 |
| 2018/0110253 | A1 * | 4/2018 | Sprenger | A23L 33/10 |
| 2018/0220690 | A1 * | 8/2018 | Berger | A61K 31/7028 |

FOREIGN PATENT DOCUMENTS

| EP | 2767173 | 8/2014 | |
| WO | WO98/43494 | * 10/1998 | ............... A23L 1/09 |
| WO | 2013025104 | 2/2013 | |
| WO | 2013057049 | 4/2013 | |

OTHER PUBLICATIONS

Chaturvedi et al., "Fucosylated human milk oligosaccharides vary between individuals and over the course of lactation" Glycobiology vol. 11 No. 5 pp. 365-372 (Year: 2001).*
Asakuma et al., "Variation of major neutral oligosaccharides levels in human colostrum" European Journal of Clinical Nutrition vol. 62, pp. 488-494 (Year: 2008).*
Bode et al., "Structure-Function Relationships of Human Milk Oligosaccharides" Advances in Nutrition vol. 3 pp. 383S-391S (Year: 2012).*
U.S. Appl. No. 15/749,527, filed Feb. 2018, Berger et al.*
De Leoz et al., "Lacto-N-Tetraose, Fucosylation, and Secretor Status Are Highly Variable in Human Milk Oligosaccharides From Women Delivering Preterm" Journal of Proteome Research (2012) vol. 11 pp. 4662-4672 (Year: 2012).*
Brandt et al., "Catch-Up Growth of Head Circumference of Very Low Birth Weight, Small for Gestational Age Preterm Infants and Mental Development to Adulthood" The Journal of Pediatrics May 2003, pp. 463-470 (Year: 2003).*
Tolsa et al., "Early Alteration of Structural and Functional Brain Development in Premature Infants Born with Intrauterine Growth Restriction" Pediatric Research vol. 56 No. 1 pp. 132-138 (Year: 2004).*
Lara-Villoslada et al., "Beneficial effects of probiotic bacteria isolated from breast milk" British Journal of Nutrition vol. 98 Suppl. 1 pp. S96-S100 (Year: 2007).*

(Continued)

*Primary Examiner* — Eric Olson

(74) *Attorney, Agent, or Firm* — K&L Gates LLP

(57) ABSTRACT

This invention relates to the use of a nutritional composition comprising Fut2-dependent oligosaccharides for promoting brain growth and development in infants in the very early postnatal period. The nutritional composition comprises Fut2-dependent oligosaccharides and Lacto-N-neotetraose and is specifically for use in promoting brain catch-up growth in preterm infants or infants with low-birth weight. The invention further relates to a kit comprising at least two of these nutritional compositions.

13 Claims, 3 Drawing Sheets

(56) References Cited

OTHER PUBLICATIONS

Bergmann et al., "Probiotics in Human Milk and Probiotic Supplementation in Infant Nutrition: a Workshop Report", British Journal of Nutrition, vol. 112, Issue No. 07, Aug. 27, 2014, pp. 1119-1128, XP055550483.

European Patent Office Communication for corresponding application No. 15786977.7-1106, dated Feb. 11, 2019, 8 pages.

* cited by examiner

COMPOSITION COMPRISING FUT2-DEPENDENT OLIGOSACCHARIDES AND LACTO-N-NEOTETRAOSE FOR USE IN PROMOTING BRAIN DEVELOPMENT AND COGNITION

CROSS REFERENCE TO RELATED APPLICATIONS

The present application is a National Stage of International Application No. PCT/EP2015/075088, filed on Oct. 29, 2015, which claims priority to European Patent Application No. 14191277.4, filed on Oct. 31, 2014, the entire contents of which are being incorporated herein by reference.

FIELD OF THE INVENTION

This invention relates to a nutritional composition comprising Fut2-dependent oligosaccharides and Lacto-N-neotetraose for use in promoting brain growth and development in infants. The invention further relates to an infant nutrition kit comprising at least two of said nutritional compositions and a use of the kit for promoting brain growth and development in infants.

BACKGROUND OF THE INVENTION

During development, especially in the first few years of life, children show interesting patterns of neural development with a high degree of neuroplasticity. The relation of brain growth and development and cognitive development is poorly understood and an area of growing research.

Some new development intends to prove a link between brain growth and cognitive development in infants and particularly in preterm infants or extremely low gestational age newborns (*J. Pediatr.* 2009; 155:344-9).

Thus, there is a great interest and need in supporting brain growth, particularly in preterm infants, to favor their cognitive and/or psychomotor development.

In particular, there is a need for a nutritional composition for use in brain growth and/or cognitive and/or psychomotor development, in particular in infants and young children, preferably infants, who were born preterm or with low-birth weight (LBW) or experienced intrauterine growth retardation (IUGR) or who suffered from growth stunting because of malnutrition, such as suboptimal intra-uterine nutrition, and/or disease.

Breast milk is the most nutritionally sound food for babies. It consists of nutrients, such as proteins, lipids, carbohydrates, minerals, vitamins, and trace elements that babies need to grow healthy. It also contains immune-related components such as IgA, leukocytes, oligosaccharides, lysozyme, lactoferrin, interferon-γ, nucleotides, cytokines, and others. Several of these compounds offer passive protection in the gastrointestinal tract and to some extent in the upper respiratory tract, preventing adherence of pathogens to the mucosa and thereby protecting the breast-fed infant against invasive infections. Human milk also contains essential fatty acids, enzymes, hormones, growth factors, polyamines, and other biologically active compounds, which may play an important role in the health benefits associated with breast-feeding.

Human milk is particularly rich in lactose based oligosaccharides. These generally non-digestible oligosaccharides are extensions of the milk sugar lactose brought about by the action of a series of glycosyltransferases such as those transferring N-acetyl-glucosamine, galactose, sialic acid or fucose. Relatively little is known on exactly which glycosyltransferase is involved in the formation of which specific milk oligosaccharide,with the exception of the two fucosyltransferases FUT2 (secretor gene) and FUT3 (Lewis gene). Both are known to be involved in the formation of the different fucosyl-oligosaccharides, because both are polymorphic with different alleles leading to null mutations and missing enzyme activity. The consequent varying enzyme activities manifest in measurable variation of specific fucosyl-oligosaccharides.

Cognitive and psychomotor development has been proposed to be promoted by supplementation with long-chain poly-unsaturated fatty acids and a number clinical trials have investigated this hypothesis. However, a recent meta-analysis that combined these data showed no significant effect of supplementation on neurodevelopment (Schulzke S M, Patole S K, Simmer K, Longchain polyunsaturated fatty acid supplementation in preterm infants (Review) *The Cochrane Library* 2011, Issue 2).

Cognitive development can be also improved in preterm infants by largely increasing the protein and energy intake (I Brandt, E. J. Sticker and M. J. Lentze, catch-up growth of head circumference of very low birth weight, small for gestational age preterm infants and mental development to adulthood, *J. Pediatr.* 2003; 142:463-8). However, large enteral feeding volumes and/or high protein/energy density of the feeds can induce intolerance to feeding. In addition, high protein intake, which leads to increased urea production, may increase the risk of renal insufficiency and metabolic acidosis in preterm infants. Furthermore, high protein/energy intake during infancy has been associated to long-term alterations on metabolic health (increased risk of obesity, type II diabetes and cardiovascular disease) (KK ONG & RJF LOOS, Rapid infancy weight gain and subsequent obesity: Systematic reviews and hopeful suggestions; Acta Paediatrica, 2006; 95: 904-908; J Rotteveel, M M van Weissenbruch, J W R Twisk, H A Delemarre-Van de Waal, Infant and Childhood Growth Patterns, Insulin Sensitivity, and Blood Pressure in Prematurely Born Young Adults Pediatrics 2008; 122: 313-321).

WO 2014/043368 and WO 2013/057049 propose methods and compositions for improving brain growth and cognitive development and for enhancing memory functions in individuals by administering human milk oligosaccharides. However, io these methods and compositions are not specifically suited for use infants or preterm infants in the very early postnatal period.

Thus, there is still a need for improved nutritional compositions for use in promoting brain growth and development in infants, and, in particular, in pre-term infants with low-birth weight (LBW) and infants who experienced intrauterine growth retardation (IUGR) or who suffered from growth stunting because of malnutrition, such as suboptimal intra-uterine nutrition, and/or disease.

Further, there is a particular need for nutritional compositions for use in infants born from mothers who are naturally expressing low levels of Fucosyltransferase 2 (Fut2). It was surprisingly found by the present inventors that the breast milk of these Fut2-deficient mothers is not only poor in Fucosyltransferase 2 (Fut2)-dependent oligosaccharides, but also comprises lower levels of other human milk oligosaccharides such as Lacto-N-Neotetraose (LNnT), as compared to the LNnT levels found in the breast milk from mothers expressing high levels of Fut2.

Thus, there is also a particular need to supplement the nutrition of infants during the lactation period in order to insure optimum levels of Fucosyltransferase 2 (Fut2)-dependent oligosaccharides and Lacto-N-Neotetraose (LNnT) during said period.

Moreover, there is a particular need for bridging the nutritional gap regarding Fucosyltransferase 2 (Fut2)-dependent oligosaccharides and Lacto-N-Neotetraose (LNnT) that may appear during the weaning period and after the stop of breast feeding. These needs are met by the subject-matter of the present invention as disclosed below.

SUMMARY OF THE INVENTION

The present inventors surprisingly found that infants who consumed breast milk containing Fucosyltransferase 2 gene (Fut2) dependent oligosaccharides and elevated levels of Lacto-N-neotetraose (LNnT) in the very early postnatal period displayed a higher head circumference growth rate. Head circumference growth rate is a proposed proxy for brain catch-up growth and development.

Accordingly, in a first aspect, the present invention provides a nutritional composition comprising Fucosyltransferase 2 (Fut2)-dependent oligosaccharides and Lacto-N-Neotetraose (LNnT) for use in promoting brain growth and development in io infants between 0 and 4 months of age, preferably in infants between 0 and 2 months of age, and more preferably in infants between 0 and 1 month of age.

In a preferred embodiment, the nutritional composition comprising Fut2-dependent oligosaccharides and Lacto-N-Neotetraose (LNnT) may be used in promoting any one of: head circumference growth rate in infants, brain catch-up growth in infants, cognitive function in infants, psychomotor development in infants, or any combination thereof, preferably wherein the infants are between 0 and 4 months of age, more preferably between 0 and 2 months of age, and most preferably between 0 and 1 month of age.

In another preferred embodiment, the nutritional composition comprising Fut2-dependent oligosaccharides and Lacto-N-Neotetraose (LNnT) may be used in providing nutrition to infants between 0 and 4 month of age, preferably to infants between 0 and 2 months of age, and more preferably to infants between 0 and 1 month of age.

In a further embodiment, the nutritional composition according to the first aspect may be administered to the infant or used in addition to breast feeding, preferably wherein the nutritional composition is administered to the infant by adding said nutritional composition to human breast milk prior to feeding the infant. Alternatively, it is preferred that the nutritional composition is administered to the infant concomitantly or alternately to breast feeding, e.g. as a stand-alone formulation.

Preferably, the nutritional composition according to the first aspect comprises Lacto-N-Neotetraose (LNnT) in an amount of from 0.1 to 0.6 g/L of composition, preferably from 0.11 to 0.55 g/L, from 0.15 to 0.5 g/L, from 0.2 to 0.45 g/L, from 0.25 to 0.4 g/L, or from 0.3 to 0.35 g/L of composition.

It is further preferred that the nutritional composition according to the first aspect comprises Fut2-dependent oligosaccharides in an amount of from 0.8 to 8.0 g/L of composition, preferably from 1.0 to 6.0 g/L, from 1.2 to 5.0 g/L, from 1.4 to 4.0 g/L, from 1.8 to 3.0 g/L, or from 2.0 to 2.2 g/L of composition.

A further preferred embodiment relates to the nutritional composition according to the first aspect of the invention, wherein the Fut2-dependent oligosaccharides are selected from 2'Fucosyllactose (2'FL), di-Fucosyllactose (diFL), and Lacto-N-fucopentaose I (LNFP I). Most preferably, the Fut2-dependent oligosaccharide is 2'Fucosyllactose (2'FL).

In another preferred embodiment, the nutritional composition according to the first aspect is an infant formula, a preterm infant formula, a human milk fortifier, a starter infant formula, a follow-on formula, a baby food formula, an infant cereal formula, a growing-up milk, a medical food product for clinical nutrition or a supplement and preferably, said composition is a preterm infant formula, a human milk fortifier, or a supplement.

In a further preferred embodiment of the first aspect of the invention, the infants were born preterm or with low-birth weight or experienced intra-uterine growth retardation or suffered from growth stunting because of malnutrition and/or disease.

In a yet further preferred embodiment of the first aspect of the invention, the infants were born from mothers who express low Fut2 activity, wherein said low Fut2 activity is characterized by a 2'Fucosyllactose concentration in the breast milk of these mothers of less than 0.2 g/L.

In a second aspect, the invention relates to the use of a nutritional composition comprising Fucosyltransferase 2 (Fut2)-dependent oligosaccharides and Lacto-N-Neotetraose (LNnT) for feeding infants between 0 and 4 month of age, preferably between 0 and 2 months of age, most preferably between 0 and 1 month of age.

A preferred embodiment relates to the use according to the second aspect, wherein the nutritional composition comprises Lacto-N-Neotetraose (LNnT) in an amount of from 0.1 to 0.6 g/L of composition, preferably from 0.11 to 0.55 g/L, from 0.15 to 0.5 g/L, from 0.2 to 0.45 g/L, from 0.25 to 0.4 g/L, or from 0.3 to 0.35 g/L of composition.

Another preferred embodiment relates to the use according to the second aspect, wherein the nutritional composition comprises Fucosyltransferase 2 (Fut2)-dependent oligosaccharides in an amount of from 0.8 to 8.0 g/L of composition, preferably from 1.0 to 6.0 g/L, from 1.2 to 5.0 g/L, from 1.4 to 4.0 g/L, from 1.8 to 3.0 g/L, or from 2.0 to 2.2 g/L of composition.

A further preferred embodiment relates to the use according to the second aspect of the invention, wherein the Fucosyltransferase 2 (Fut2)-dependent oligosaccharides io are selected from 2'Fucosyllactose (2'FL), di-Fucosyllactose (diFL), and Lacto-N-fucopentaose I (LNFP I). Most preferably, the Fucosyltransferase 2 (Fut2)-dependent oligosaccharides are 2'Fucosyllactose (2'FL).

In another preferred embodiment of the use according to the second aspect, the nutritional composition is an infant formula, a preterm infant formula, a human milk fortifier, a starter infant formula, a follow-on formula, a baby food formula, an infant cereal formula, a growing-up milk, a medical food product for clinical nutrition or a supplement and preferably, said composition is a preterm infant formula, a human milk fortifier, or a supplement.

In a further preferred embodiment of the second aspect, the nutritional composition may be used in addition to breast feeding. Preferably, the nutritional composition is administered to the infant by adding said nutritional composition to human breast milk prior to feeding the infant. Alternatively, it is preferred that the nutritional composition is administered to the infant concomitantly or alternately to breast feeding, e.g. as a stand-alone formulation.

In yet another preferred embodiment of the use according to the second aspect, the infants were born preterm or with low-birth weight or experienced intra-uterine growth retardation or suffered from growth stunting because of malnutrition and/or disease.

In another preferred embodiment of the second aspect of the invention, the infants were born from mothers who express low Fut2 activity, wherein said low Fut2 activity is characterized by a 2'Fucosyllactose concentration in the breast milk of these mothers of less than 0.2 g/L.

In a third aspect, the invention relates to the use of a nutritional composition comprising Fucosyltransferase 2 (Fut2)-dependent oligosaccharides and Lacto-N-Neotetraose (LNnT) for promoting any one of: brain growth and development in infants, head circumference growth rate in infants, brain catch-up growth in infants, cognitive function in infants, psychomotor development in infants, or any combination thereof, preferably wherein the infants are between 0 and 4 months of age, more preferably wherein the infants are between 0 and 2 months of age, and most preferably wherein the infants are between 0 and 1 month of age.

A preferred embodiment relates to the use according to the third aspect, wherein the io nutritional composition comprises Lacto-N-Neotetraose (LNnT) in an amount of from 0.1 to 0.6 g/L of composition, preferably from 0.11 to 0.55 g/L, from 0.15 to 0.5 g/L, from 0.2 to 0.45 g/L, from 0.25 to 0.4 g/L, or from 0.3 to 0.35 g/L of composition.

Another preferred embodiment relates to the use according to the third aspect, wherein the nutritional composition comprises Fucosyltransferase 2 (Fut2)-dependent oligosaccharides in an amount of from 0.8 to 8.0 g/L of composition, preferably from 1.0 to 6.0 g/L, from 1.2 to 5.0 g/L, from 1.4 to 4.0 g/L, from 1.8 to 3.0 g/L, or from 2.0 to 2.2 g/L of composition.

A further preferred embodiment relates to the use according to the third aspect of the invention, wherein the Fucosyltransferase 2 (Fut2)-dependent oligosaccharides are selected from 2'Fucosyllactose (2'FL), di-Fucosyllactose (diFL), and Lacto-N-fucopentaose I (LNFP I). Most preferably, the Fucosyltransferase 2 (Fut2)-dependent oligosaccharides are 2'Fucosyllactose (2'FL).

In another preferred embodiment of the use according to the third aspect, the nutritional composition is an infant formula, a preterm infant formula, a human milk fortifier, a starter infant formula, a follow-on formula, a baby food formula, an infant cereal formula, a growing-up milk, a medical food product for clinical nutrition or a supplement and preferably, said composition is a preterm infant formula, a human milk fortifier, or a supplement.

In a further preferred embodiment of the third aspect, the nutritional composition may be used in addition to breast feeding, Preferably, the nutritional composition is administered to the infant by adding said nutritional composition to human breast milk prior to feeding the infant. Alternatively, it is preferred that the nutritional composition is administered to the infant concomitantly or alternately to breast feeding, e.g. as a stand-alone formulation.

In yet another preferred embodiment of the use according to the third aspect, the infants were born preterm or with low-birth weight or experienced intra-uterine growth retardation or suffered from growth stunting because of malnutrition and/or disease.

In a yet further preferred embodiment of the third aspect of the invention, the infants were born from mothers who express low Fut2 activity, wherein said low Fut2 activity is characterized by a 2'Fucosyllactose concentration in the breast milk of these mothers of less than 0.2 g/L.

In a fourth aspect, the invention relates to an infant nutrition kit comprising: at least one nutritional composition A for infants between 0 up to 1 month of age, and at least one nutritional composition B for infants above 1 month and up to 2 months of age, wherein each one of the nutritional compositions A and B comprises a combination of Fucosyltransferase 2 (Fut2)-dependent oligosaccharides and Lacto-N-Neotetraose (LNnT), and wherein said nutritional compositions A and B differ from each other in the amount of Fucosyltransferase 2 (Fut2)-dependent oligosaccharides and Lacto-N-Neotetraose (LNnT) present therein.

Preferably, said kit further comprises at least one nutritional composition C for infants above 2 months and up to 4 months of age, more preferably wherein the at least one nutritional composition C comprises a combination of Fucosyltransferase 2 (Fut2)-dependent oligosaccharides and Lacto-N-Neotetraose (LNnT), and even more preferably wherein nutritional compositions A, B and C differ from each other in the amount of Fucosyltransferase 2 (Fut2)-dependent oligosaccharides and Lacto-N-Neotetraose (LNnT) present therein.

In a preferred embodiment of the kit according to the fourth aspect, the amounts of Fucosyltransferase 2 (Fut2)-dependent oligosaccharides and Lacto-N-Neotetraose (LNnT) present in each nutritional composition are selected according to the age of the infants.

In a further preferred embodiment of said kit, the amounts of Fucosyltransferase 2 (Fut2)-dependent oligosaccharides and Lacto-N-Neotetraose (LNnT) present in the at least one nutritional composition A exceed the amounts of Fucosyltransferase 2 (Fut2)-dependent oligosaccharides and Lacto-N-Neotetraose (LNnT) present in the at least one nutritional composition B. It is also preferred that the amounts of Fucosyltransferase 2 (Fut2)-dependent oligosaccharides and Lacto-N-Neotetraose (LNnT) present in the at least one nutritional composition B exceed the amounts of Fucosyltransferase 2 (Fut2)-dependent oligosaccharides and Lacto-N-Neotetraose (LNnT) present in the at least one nutritional composition C.

In a yet further preferred embodiment of said kit, the Fucosyltransferase 2 (Fut2)-dependent oligosaccharides are selected from 2'Fucosyllactose (2'FL), di-Fucosyllactose (diFL), and Lacto-N-fucopentaose I (LNFP I). More preferably, the Fucosyltransferase 2 (Fut2)-dependent oligosaccharides are 2'Fucosyllactose (2'FL).

In another preferred embodiment of said kit, Fucosyltransferase 2 (Fut2)-dependent oligosaccharides are present in a nutritional composition in an amount of from 0.8 to 8.0 g/L of composition, preferably from 1.0 to 6.0 g/L, from 1.2 to 5.0 g/L, from 1.4 to 4.0 g/L, from 1.8 to 3.0 g/L, or from 2.0 to 2.2 g/L of composition. It is also preferred that Lacto-N-Neotetraose (LNnT) is present in a nutritional composition in an amount of from 0.1 to 0.6 g/L of composition, preferably from 0.11 to 0.55 g/L, from 0.15 to 0.5 g/L, from 0.2 to 0.45 g/L, from 0.25 to 0.4 g/L, or from 0.3 to 0.35 g/L of composition.

It is particularly preferred that Fucosyltransferase 2 (Fut2)-dependent oligosaccharides are present in the at least one nutritional composition A in an amount of from 1.8 to 8.0 g/L of composition, preferably from 2.0 to 6.0 g/L and more preferably from 2.2 to 5.0 g/L of composition. It is further preferred that Fucosyltransferase 2 (Fut2)-dependent oligosaccharides are present in the at least one nutritional composition B in an amount of from 1.2 to 4.0 g/L of composition, preferably from 1.4 to 3.0 g/L and more preferably from 1.8 to 2.2 g/L of composition. It is further preferred that Fucosyltransferase 2 (Fut2)-dependent oligosaccharides are present in the at least one nutritional composition C in an amount of from 0.8 to 2.2 g/L of composition, preferably from 1.0 to 2.0 g/L and more preferably from 1.4 to 1.8 g/L of composition.

It is also particularly preferred that Lacto-N-Neotetraose (LNnT) is present in the at least one nutritional composition A in an amount of from 0.15 to 0.6 g/L of composition, preferably from 0.2 to 0.55 g/L and more preferably from 0.25 to 0.5 g/L of composition. It is further preferred that Lacto-N-Neotetraose (LNnT) is present in the at least one nutritional composition B in an amount of from 0.11 to 0.55 g/L of composition, preferably from 0.15 to 0.35 g/L and more preferably from 0.2 to 0.3 g/L of composition. It is further preferred that Lacto-N-Neotetraose (LNnT) is present in the at least one nutritional composition C in an amount of from 0.1 to 0.5 g/L of composition, preferably from 0.11 to 0.25 g/L and more preferably from 0.15 to 0.2 g/L of composition.

A further embodiment of the invention relates to the infant nutrition kit according to the fourth aspect for use in promoting any one of: brain growth and development in io infants, head circumference growth rate in infants, brain catch-up growth in infants, cognitive function in infants, psychomotor development in infants, or any combination thereof, wherein the at least one nutritional composition A is used in infants between 0 up to 1 month of age, and the at least one nutritional composition B is used in infants above 1 month and up to 2 months of age, and, optionally, the at least one nutritional composition C is used in infants above 2 months and up to 4 months of age.

A further embodiment of the invention relates to the infant nutrition kit according to the fourth aspect for use in providing nutrition to an infant, wherein at least one nutritional composition A is used in infants between 0 up to 1 month of age, and at least one nutritional composition B is used in infants above 1 month and up to 2 months of age, and, optionally, at least one nutritional composition C is used in infants above 2 months and up to 4 months of age.

In a fifth aspect, the invention relates to the use of the infant nutrition kit according to the fourth aspect in promoting any one of: brain growth and development in infants head circumference growth rate in infants, brain catch-up growth in infants, cognitive function in infants, psychomotor development in infants, or any combination thereof, wherein the at least one nutritional composition A is used in infants between 0 up to 1 month of age, and the at least one nutritional composition B is used in infants above 1 month and up to 2 months of age, and, optionally, the at least one nutritional composition C is used in infants above 2 months and up to 4 months of age.

In a sixth aspect, the invention relates to the use of the infant nutrition kit according to the fourth aspect for providing nutrition to an infant, wherein the at least one nutritional composition A is used in infants between 0 up to 1 month of age, and the at least one nutritional composition B is used in infants above 1 month and up to 2 months of age, and, optionally, the at least one nutritional composition C is used in infants above 2 months and up to 4 months of age.

Other aspects and embodiments of the present invention are described below.

DETAILED DESCRIPTION OF THE INVENTION

Figure 1A:
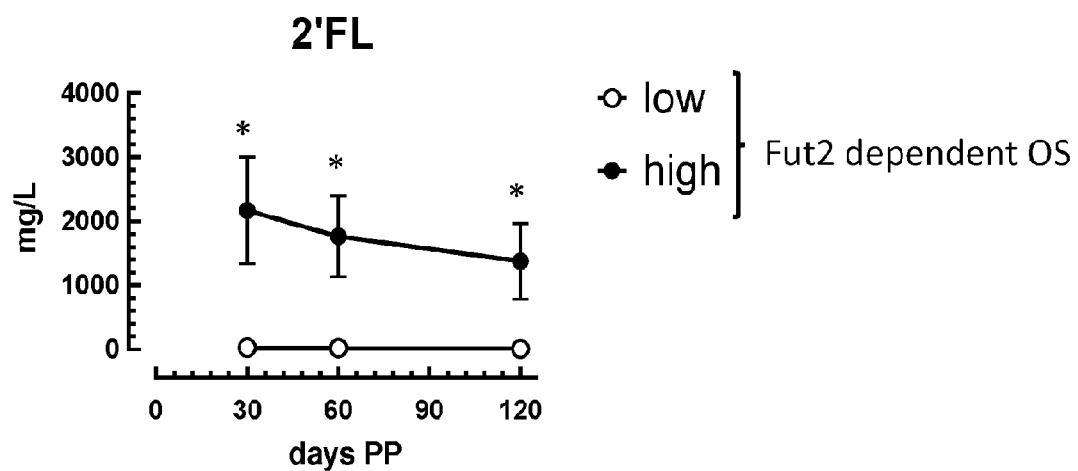
FIG. 1a depicts 2'Fucosyllactose (2'FL) levels in milk with high (closed circles) and low (open circles) Fucosyltransferase 2 (Fut2)-dependent milk oligosaccharides (OS) at 30, 60 and 120 days post partum (PP). * Indicate significant difference by t-test at specific day PP.

The present inventors surprisingly found that the use of a specific combination of Fucosyltransferase 2 (Fut2)-dependent oligosaccharides and Lacto-N-Neotetraose (LNnT) in the very early postnatal period of infant nutrition is highly effective in promoting head circumference growth rate, brain growth and development, brain catch-up growth, cognitive function, and psychomotor development in these infants.

Therefore, the present invention provides a nutritional composition comprising Fucosyltransferase 2 (Fut2)-dependent oligosaccharides and Lacto-N-Neotetraose (LNnT) for use in promoting brain growth and development in infants between 0 and 4 month of age.

Infants

In the context of the present invention, the term "infant" or "infants" means children under the age of 12 months. Preferably, the nutritional composition of the invention is used in infants between 0 and 4 months of age, more preferably in infants between 0 and 2 months of age, and most preferably in infants between 0 and 1 month of age.

The expressions "between 0 up to 1 month", "between birth up to 1 month", "from birth up to 1 month", "up to 1 month post partum", "between birth up to 30 days", "from birth up to 30 days", "between 0 up to 30 days post partum", and "up to 30 days post partum" can be used interchangeably.

Accordingly, the expressions "between 0 up to 2 month", "between birth up to 2 month", "from birth up to 2 month", "up to 2 month post partum", "between birth up to 60 days", "from birth up to 60 days", "between 0 up to 60 days post partum", and "up to 60 days post partum" can be used interchangeably.

Also accordingly, the expressions "between 0 up to 4 month", "between birth up to 4 month", "from birth up to 4 month", "up to 4 month post partum", "between birth up to 120 days", "from birth up to 120 days", "between 0 up to 120 days post partum", and "up to 120 days post partum" can be used interchangeably.

The term "preterm infant" (or "premature infant") means an infant born at less than 37 weeks of gestational age.

The term "low birth weight infant" or "LBW" means an infant having a liveborn weight of less than 2,500 g.

Human Milk Oligosaccharides

The present inventors surprisingly found that infants who consumed breast milk from mothers who show a strong expression of the Fucosyltransferase 2 gene (Fut2) displayed a higher head circumference growth rate in the very early postnatal period. Head circumference growth rate is a proposed proxy for brain catch-up growth and development.

Genetic polymorphism of the Fucosyltransferase 2 gene (Fut2) of the mother controls 2'fucosylation of oligosaccharides in human breast milk. The prototype of Fucosyltransferase 2 (Fut2)-dependent milk oligosaccharides is 2'Fucosyllactose (2'FL). Among other Fucosyltransferase 2 (Fut2)-dependent milk oligosaccharides is di-fucosyllactose (diFL) and Lacto-N-fucopentaose I (LNFP I). Some genotypes were found to express hardly any 2'Fucosyllactose (2'FL), while others express 2'FL at around 2 g/l and up to 5 g/L.

In the context of the present invention, "high Fucosyltransferase 2 (Fut2) expression", "high Fut2 activity", "strong expression of the Fucosyltransferase 2 gene (Fut2)", or "high Fucosyltransferase 2 (Fut2)-dependent milk oligosaccharides" means that the concentration of 2'Fucosyllactose in breast milk is above 0.2 g/L.

Further, in the present context, "low Fucosyltransferase 2 (Fut2) expression", "low Fut2 activity", or "low Fucosyltransferase 2 (Fut2)-dependent milk oligosaccharides" means that the concentration of 2'Fucosyllactose in breast milk is 0.2 g/L or less than 0.2 g/L.

It was further found by the present inventors that strong expression of the Fucosyltransferase 2 gene (Fut2) goes along with elevated levels of Lacto-N-neotetraose (LNnT) in milk. In particular, lower levels of Lacto-N-neotetraose (LNnT) were found in milk with low levels of Fut2 dependent milk oligosaccharides, whereas high levels of Lacto-N-neotetraose (LNnT) were found in milk with high levels of Fut2 dependent milk oligosaccharides.

Thus, the nutritional composition of the invention providing Fucosyltransferase 2 (Fut2)-dependent oligosaccharides and Lacto-N-Neotetraose (LNnT) advantageously mimics the composition of breast milk from mothers who show a strong expression of the Fucosyltransferase 2 gene (Fut2)/high Fut2 activity. Therefore, the inventive composition is specifically suited to promote head circumference growth rate, brain growth and development, brain catch-up growth, cognitive function, and psychomotor development in infants, and, in particular, in infants who were born preterm or with low-birth weight or experienced intra-uterine growth retardation or suffered from growth stunting because of malnutrition and/or disease.

The present nutritional composition is also specifically suited for use in infants who were born from mothers with low Fut2 activity. It was surprisingly found by the present inventors that the breast milk of Fut2-deficient mothers is not only poor in Fucosyltransferase 2 (Fut2)-dependent oligosaccharides, but also comprises lower levels of Lacto-N-Neotetraose (LNnT) as compared to the LNnT levels found in the breast milk from mothers with high Fut2 activity.

Without wishing to be bound by theory, it is believed that the effects of the present nutritional composition on brain growth and development, cognitive function, and psychomotor development in infants is based on a synergistic action of Fucosyltransferase 2 (Fut2)-dependent oligosaccharides and Lacto-N-Neotetraose (LNnT). In particular, it is believed that L-fucose derived from Fucosyltransferase 2 (Fut2)-dependent oligosaccharides acts on brain longterm potentiation for memory consolidation especially during sleep, while at the same time Fucosyltransferase 2 (Fut2)-dependent oligosaccharides and LNnT affect bifidobacteria and their metabolism, which in turn affects brain growth and development.

Preferably, the Fucosyltransferase 2 (Fut2)-dependent oligosaccharides are selected from 2'Fucosyllactose (2'FL), di-Fucosyllactose (diFL) and Lacto-N-fucopentaose I (LNFP I) and preferably are 2'Fucosyllactose (2'FL).

2'Fucosyllactose ("2'FL" or "2FL"), di-Fucosyllactose ("diFL") and Lacto-N-fucopentaose I ("LNFP I") belong to the group of neutral oligosaccharides. The term "neutral oligosaccharide" means an oligosaccharide having no charge.

The named fucosylated oligosaccharides may be isolated by chromatography or filtration technology from a natural source such as animal milks. Alternatively, they may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

Preferably, the Fucosyltransferase 2 (Fut2)-dependent oligosaccharides may be used in the nutritional composition of the invention in an amount of from 0.8 to 8.0 g/L of composition. The Fucosyltransferase 2 (Fut2)-dependent oligosaccharides may be also used in an amount of from 1.0 to 6.0 g/L, from 1.2 to 5.0 g/L, from 1.4 to 4.0 g/L, from 1.8 to 3.0 g/L, or from 2.0 to 2.2 g/L of composition.

In a preferred embodiment, the Fucosyltransferase 2 (Fut2)-dependent oligosaccharides are 2'Fucosyllactose (2'FL). 2'FL may be used in an amount of from 0.8 to 8.0 g/L, from 1.0 to 6.0 g/L, from 1.2 to 5.0 g/L, from 1.4 to 4.0 g/L, from 1.8 to 3.0 g/L, or from 2.0 to 2.2 g/L of composition. It is particularly preferred that 2'FL is used in the nutritional composition of the invention in an amount of from 1.0 to 5.0 g/L of composition.

Lacto-N-Neotetraose (LNnT) is an N-acetylated oligosaccharide. The term "N-acetylated" oligosaccharide means an oligosaccharide having at least one hexose carrying an N-acetyl residue.

Lacto-N-Neotetraose (LNnT) may be synthesized by enzymatic transfer of saccharide units from donor moieties to receptor moieties using glycosylhydrolases and/or glycosyltransferases as described for example in U.S. Pat. No. 5,288,637 and WO 96/10086. Alternatively, LNnT may be prepared by chemical conversion of ketohexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably, Lacto-N-Neotetraose (LNnT) may be used in the nutritional composition of the invention in an amount of from 0.1 to 0.6 g/L of composition, preferably from 0.11 to 0.55 g/L, from 0.15 to 0.5 g/L, from 0.2 to 0.45 g/L, from 0.25 to 0.4 g/L, or from 0.3 to 0.35 g/L of composition.

In a particularly preferred embodiment, Lacto-N-Neotetraose (LNnT) is used in the nutritional composition of the invention in an amount of about 0.5 g/L of composition, and 2'Fucosyllactose (2'FL) is used in the nutritional composition of the invention in an amount of about 1 g/L of composition.

The oligosaccharide combination of the nutritional composition according to the invention can be the only source of oligosaccharides in the composition.

Use of the Nutritional Composition of the Invention

The nutritional composition described herein may be used in promoting any one of head circumference growth rate, brain growth, brain catch-up growth, brain development, cognitive function, and psychomotor development in infants.

It was surprisingly found by the present inventors that the effect of the nutritional composition of the invention on brain growth and development in infants was strongest in the very early postnatal period of the infants, i.e. in the period of from 0 up to 4 months post partum, more particularly in the period of from 0 up to 2 months post partum, and most particularly in the period of from 0 up to 1 month post partum.

Therefore, the present nutritional composition may be typically used from 0 up to 4 months after infant's birth, from 0 up to 2 months after infant's birth, or from 0 up to 1 month after infant's birth. Preferably, the nutritional composition may be used in the period of from 0 up to 1 month after infant's birth.

In this period, the present nutritional composition may be generally used for feeding infants or for providing nutrition to infants.

The present nutritional composition may be specifically used in infants who were born preterm or with low birth weight (LBW) or experienced intra-uterine growth retardation (IUGR) or who suffered from growth stunting due to disease and/or malnutrition. Preferably, the present composition is used in preterm infants.

In all of the above-mentioned applications and uses, the present nutritional composition may be used either as a complete substitute for human breast milk, or in addition to breast feeding during the lactation period.

In an embodiment wherein the present nutritional composition is used in addition to breast feeding, human breast milk may be supplemented with the present nutritional composition prior to feeding the infant. Therefore, human breast milk may be naturally derived from an infant's mother, admixed with the present nutritional composition and fed to the infant via flask.

Alternatively, the present nutritional composition may be used concomitantly or alternately to breast feeding. In this case, the present nutritional composition is used as a stand-alone formulation. Such a stand-alone formulation may be either a full meal replacement such as a nutritionally complete formula or it may be a supplement. When the present nutritional composition is administered to the infant concomitantly with breast feeding, said composition preferably is a supplement which may be administered to the infant prior to or after breast feeding, for instance from 1 to 12, from 2 to 10, from 3 to 8, or from 4 to 6 times per day.

When the present nutritional composition is administered to the infant alternately with breast feeding, said composition preferably is a full meal replacement, and more preferably a nutritionally complete infant formula, which is administered to the infant instead of breast feeding, for instance from 1 to 12, from 2 to 10, from 3 to 8, or from 4 to 6 times per day.

The present nutritional composition may also be administered to the infant after a period of exclusive breast feeding and during the weaning period until the end of the lactation period in alternate or concomitant manner. Preferably, the frequency of feeding the present nutritional composition increases, while the frequency of breast feeding decreases during the weaning period until the end of the lactation period.

Supplementing an infant with the composition of the invention during the breast feeding/lactation period, either by adding said composition directly to breast milk prior to feeding the infant, or by administering the composition as a stand-alone formulation in addition to breast feeding, is particularly advantageous in infants born from mothers who express low or no Fucosyltransferase 2 (Fut2) and who therefore provide low levels of Fucosyltransferase 2 (Fut2)-dependent oligosaccharides and/or low levels of Lacto-N-Neotetraose LNnT in their breast milk.

The present nutritional composition may preferably be added to human breast milk or administered to the infant concomitantly or alternately to breast feeding in an amount that is sufficient to mimic the natural levels of Fucosyltransferase 2 (Fut2)-dependent oligosaccharides and Lacto-N-Neotetraose (LNnT) in the breast milk of mothers with high Fut2 activity. Within the present context, "high Fut2 activity" means that the concentration of 2'Fucosyllactose in human breast milk is above 0.2 g/L. For instance, said natural levels of Fucosyltransferase 2 (Fut2)-dependent oligosaccharides in the breast milk of mothers with high Fut2 activity are above 0.2 g/L and up to about 8 g/L, including 2'Fucosyllactose (2'FL), di-Fucosyllactose (diFL) and Lacto-N-fucopentaose I (LNFP I). The natural levels of 2-Fucosyllactose (2'FL) in the breast milk of mothers with high Fut2 activity are up to about 5 g/L.

The natural levels of Lacto-N-Neotetraose (LNnT) in the breast milk of mothers with high Fut2 activity were found to be up to about 0.6 g/L.

Nutritional Compositions

As used herein, the expressions "composition(s)" and "nutritional composition(s)" are sought to refer to the nutritional composition for use in the present invention.

In the present context, a nutritional composition may be any kind of composition that provides a nutritional benefit to an individual and that may be safely consumed by a human or animal. It may be in solid, semi-solid or liquid form and may comprise one or more macronutrients, micronutrients, food additives, water, etc. For instance, the nutritional composition may comprise the following macronutrients: a source of proteins, a source of lipids, a source of carbohydrates and any combination thereof. Furthermore, the nutritional composition may comprise the following micronutrients: vitamins, minerals, fiber, phytochemicals, antioxidants, prebiotics, probiotics, and any combination thereof. The composition may also contain food additives such as stabilizers (when provided in solid form) or emulsifiers (when provided in liquid form).

The nutritional composition generally contains a protein source. The protein can be in an amount of from 1.6 to 3 g per 100 kcal, such as below 2.0 g per 100 kcal, e.g. between 1.8 to 2 g per 100kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed. In one particular embodiment the proteins of the composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition is a hypoallergenic nutritional composition. The term "hypoallergenic composition" means a composition which is unlikely to cause allergic reactions.

The nutritional composition generally contains a carbohydrate source. This is particularly preferable in the case where the nutritional composition of the invention is an infant formula. In this case, any carbohydrate source conventionally found in infant formulae such as lactose, sucrose, maltodextrin, starch and mixtures thereof may be used although one of the preferred sources of carbohydrates is lactose.

The nutritional composition generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and a-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition may contain emulsifiers and stabilisers such as soy, lecithin, citric acid esters of mono- and diglycerides, and the like.

The nutritional composition may contain probiotics. The term "probiotic" means microbial cell preparations or components of microbial cells with a beneficial effect on the health or well-being of the host. (Salminen S, Ouwehand A. Benno Y. et al. "Probiotics: how should they be defined" Trends Food Sci. Technol. 1999:10 107-10). The microbial cells are generally bacteria or yeasts.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp. In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium* breve sold by Institut RoseII (Lallemand) under the trademark R0070.

The nutritional composition may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition can further comprise at least one non-digestible oligosaccharide (e.g. prebiotics) other than the human milk oligosaccharides previously mentioned. Examples of prebiotics include certain oligosaccharides, such as fructooligosaccharides (FOS), galactooligosaccharides (GOS) and/or bovine's milk derived oligosaccharides (BMOs). They are usually in an amount between 0.3 and 10% by weight of composition.

Generally, the nutritional composition may be in the form of a nutritional product, preferably a food product, a nutritional supplement, a full meal, a nutritionally complete formula, a pharmaceutical formulation, functional food, a beverage product, and combinations thereof.

Preferably, the nutritional composition of the invention is an infant formula, a preterm infant formula, a human milk fortifier, a starter infant formula, a follow-on formula, a baby food formula, a medical food product for clinical nutrition or a supplement.

In a particularly preferred embodiment the nutritional composition is a preterm infant formula, a human milk fortifier, or a supplement.

In the context of the invention, the term expression "infant formula" means a nutritional product intended for particular nutritional use by infants during the first 12 months of life, which satisfies the nutritional requirements of said infants. It has to be understood that an infant formula can be either a complete or a partial substitute for human milk, i.e. that infants can be fed with the infant formula alone, or that the infant formula can be used as a complement of human milk. For further details on infant formulae it is referred to the Commission Directives 2006/141/EC of 22 Dec. 2006 and/or 91/321/EEC of 14 May. 1991 on infant formulae and follow-on formulae, Article 1.2 (c). The expression "infant formula" encompasses both "starter infant formula", i.e. a foodstuff intended for particular nutritional use by infants during the first four months of life and the "follow-on formula", i.e. a foodstuff intended for particular nutritional use by infants aged over four months and constituting the principal liquid element in the progressively diversified diet of this category of person.

The term "preterm infant formula" means an infant formula intended for a preterm infant.

The term "human milk fortifier" means a supplement used to increase the calories, protein, minerals and vitamins in breast milk fed to preterm infants or infants with a low birth weight.

The term "baby food formula" means a foodstuff intended for particular nutritional use by infants during the first years of life.

A "supplement" is typically to be used during hospital stay and/or to be used after hospital discharge. A supplement can be for a preterm infant or a child or an adult.

Said supplement is preferably a product for preterm feeding such as a preterm infant formula, a human milk fortifier, or a preterm infant supplement. It may be in the form of powder, tablets, capsules, pastilles or a liquid for example. The supplement may further contain protective hydrocolloids (such as gums, proteins , modified starches), binders , film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

In a preferred embodiment, the supplement may be added to human breast milk that is naturally derived from the infant's mother. Supplementation of natural human breast milk with the composition of the invention is particularly advantageous in infants born from mothers who express low or no Fucosyltransferase 2 (Fut2) and who therefore provide low levels of Fucosyltransferase 2 (Fut2)-dependent oligosaccharides and/or low levels of Lacto-N-Neotetraose LNnT in their breast milk. The supplement may preferably be added to human breast milk in an amount that is sufficient to mimic the natural levels of Fucosyltransferase 2 (Fut2)-dependent oligosaccharides and Lacto-N-Neotetraose (LNnT) in the breast milk of mothers with high Fut2 activity as seen in 2'Fucosyllactose levels above 0.2 g/L of milk. For instance, said natural levels of Fucosyltransferase 2 (Fut2)-dependent oligosaccharides in the breast milk of mothers with high Fut2 activity are up to about 8 g/L, wherein the natural levels of 2-Fucosyllactose (2'FL) in the breast milk of mothers with high Fut2 activity are up to about 5 g/L. The natural levels of Lacto-N-Neotetraose (LNnT) in the breast milk of mothers with high Fut2 activity are up to about 0.6 g/L.

The supplement can also be added in a product acceptable to the infant, such as an ingestible carrier or support, respectively. Examples of such carriers or supports are pharmaceutical compositions, food compositions or pet food compositions. Non-limiting examples for such compositions are milk, yogurt, curd, cheese, fermented milks, milk based fermented products, fermented cereal based products, milk based powders, human milk, infant formula, preterm infant formula, starter infant formula, follow-on formula, baby food formula, a medical food product for clinical nutrition, oral supplement, and tube feeding. Further, the supplement may contain an organic or inorganic carrier material suitable for enteral or parenteral administration as well as vitamins, minerals trace elements and other micronutrients in accordance with the recommendations of Government bodies such as the USRDA.

In another preferred embodiment, the nutritional composition is a synthetic nutritional composition (i.e. not breast milk). The expression "synthetic nutritional composition" means a synthetic mixture obtained by chemical and/or biological means, which may be chemically identical to the mixture naturally occurring in mammalian milks.

The composition according to the invention can also be a product for children or adults such as yogurt or medical food, as well as a pet food product.

Method for Manufacturing the Nutritional Composition of the Invention

The nutritional composition may be prepared in any suitable manner known in the art. For example, it may be prepared by blending together a protein source, a carbohydrate source (different from the oligosaccharide combination), and a fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50 [deg.] C. and about 80 [deg.] C. to aid dispersal of the ingredients. Commercially available liquefiers may be used to form the liquid mixture. The Fucosyltransferase 2 (Fut2)-dependent oligosaccharides and Lacto-N-Neotetraose will be added at this stage if the final product is to have a liquid form. If the final product is to be a powder, the Fucosyltransferase 2 (Fut2)-dependent oligosaccharides and Lacto-N-Neotetraose may likewise be added at this stage if desired. The liquid mixture is then homogenised, for example in two stages.

The liquid mixture may then be thermally treated to reduce bacterial loads, by rapidly heating the liquid mixture to a temperature in the range between about 80 [deg.] C. and about 150 [deg.] C. for a duration between about 5 seconds and about 5 minutes, for example. This may be carried out by means of steam injection, an autoclave or a heat exchanger, for example a plate heat exchanger.

Then, the liquid mixture may be cooled to between about 60 [deg.] C. and about 85 [deg.] C. for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point. The homogenized mixture is transferred to a suitable drying apparatus such as a spray dryer or freeze dryer and converted to powder. The powder should have a moisture content of less than about 5% by weight. The Fucosyltransferase 2 (Fut2)-dependent oligosaccharides and Lacto-N-Neotetraose may be added at this stage by dry-mixing, or by blending them in a syrup form of crystals and spray-dry (or freeze-dry).

If a liquid composition is preferred, the homogenized mixture may be sterilized then aseptically filled into suitable containers or may be first filled into the containers and then retorted.

In an embodiment, the nutritional composition of the invention may be a supplement in an amount sufficient to achieve the desired effect of brain growth and development in an infant. This form of administration is particularly suited for preterm or LBW or IUGR infants.

The amount of Fucosyltransferase 2 (Fut2)-dependent oligosaccharides and Lacto-N-Neotetraose to be included in the supplement will be selected according to the manner in which the supplement is to be administered.

For instance, Lacto-N-Neotetraose (LNnT) may be included into the nutritional composition of the invention in an amount of from 0.1 to 0.6 g/L of composition, and preferably in an amount of from 0.11 to 0.55 g/L, from 0.15 to 0.5 g/L, from 0.2 to 0.45 g/L, from 0.25 to 0.4 g/L, or from 0.3 to 0.35 g/L of composition.

Fut2-dependent oligosaccharides may be included into the nutritional composition of the invention in an amount of from 0.8 to 8.0 g/L of composition, and preferably in an amount from 1.0 to 6.0 g/L, from 1.2 to 5.0 g/L, from 1.4 to 4.0 g/L, from 1.8 to 3.0 g/L, or from 2.0 to 2.2 g/L of composition.

Infant Nutrition Kit

The inventors further found that the need for both, Fucosyltransferase 2 (Fut2)-dependent oligosaccharides and Lacto-N-Neotetraose in infants decrease with time as determined after 30, 60 and 120 days after infants' birth.

Therefore, the present invention further relates to an infant nutrition kit comprising at least two nutritional compositions that differ from each other in the amounts of Fucosyltransferase 2 (Fut2)-dependent oligosaccharides and Lacto-N-Neotetraose comprised therein. Preferably, said kit comprises a set of nutritional compositions according to the invention.

For instance, such a kit may comprise at least one first nutritional composition A for infants between 0 up to 1 month of age, preferably in a quantity that is sufficient for feeding a newly born infant from its birth and up to 1 month of age. Said first nutritional composition A preferably comprises a combination of Fucosyltransferase 2 (Fut2)-dependent oligosaccharides and Lacto-N-Neotetraose (LNnT).

The amounts of Fucosyltransferase 2 (Fut2)-dependent oligosaccharides and Lacto-N-Neotetraose (LNnT) present in the at least one nutritional composition A are typically selected according to the age of the infants.

For instance, Fucosyltransferase 2 (Fut2)-dependent oligosaccharides are comprised in a first nutritional composition A in an amount of from 1.8 to 8.0 g/L of composition, preferably from 2.0 to 6.0 g/L and more preferably from 2.2 to 5.0 g/L of composition. It is also preferred that Lacto-N-Neotetraose (LNnT) is comprised in a first nutritional composition A in an amount of from 0.15 to 0.6 g/L of composition, preferably from 0.2 to 0.55 g/L and more preferably from 0.25 to 0.5 g/L of composition.

The kit may further comprise one or more of a second nutritional composition B for infants above 1 month and up to 2 months of age, preferably in a quantity that is sufficient for feeding an infant from 1 month and up to 2 month of age. Said second nutritional composition B preferably comprises a combination of Fucosyltransferase 2 (Fut2)-dependent oligosaccharides and Lacto-N-Neotetraose (LNnT). Typically, nutritional compositions A and B differ from each other in the amount of Fucosyltransferase 2 (Fut2)-dependent oligosaccharides and Lacto-N-Neotetraose (LNnT) present therein, more typically such that the amounts of Fucosyltransferase 2 (Fut2)-dependent oligosaccharides and Lacto-N-Neotetraose (LNnT) present in the at least one nutritional composition A exceed the individual and total amounts of Fucosyltransferase 2 (Fut2)-dependent oligosaccharides and Lacto-N-Neotetraose (LNnT) present in the at least one nutritional composition B, respectively.

Preferably, the amounts of Fucosyltransferase 2 (Fut2)-dependent oligosaccharides and Lacto-N-Neotetraose (LNnT) present in the at least one nutritional composition B are selected according to the age of the infants.

Typically, Fucosyltransferase 2 (Fut2)-dependent oligosaccharides are comprised in a nutritional composition B in an amount of from 1.2 to 4.0 g/L of composition, preferably from 1.4 to 3.0 g/L and more preferably from 1.8 to 2.2 g/L of composition. It is also preferred that Lacto-N-Neotetraose (LNnT) is comprised in a nutritional composition B in an amount of from 0.11 to 0.55 g/L of composition, preferably from 0.15 to 0.35 g/L and more preferably from 0.2 to 0.3 g/L of composition.

The kit may further comprise one or more of a third nutritional composition C for infants above 2 months and up to 4 months of age, preferably in a quantity that is sufficient for feeding an infant from 2 month and up to 4 month of age. Also said third nutritional composition C preferably comprises a combination of Fucosyltransferase 2 (Fut2)-dependent oligosaccharides and Lacto-N-Neotetraose (LNnT). Typically, nutritional compositions A, B and C differ from each other in the amount of Fucosyltransferase 2 (Fut2)-dependent oligosaccharides and Lacto-N-Neotetraose (LNnT) present therein, more typically such that the amounts of Fucosyltransferase 2 (Fut2)-dependent oligosaccharides and Lacto-N-Neotetraose (LNnT) present in the at least one nutritional composition A exceed the amounts of Fucosyltransferase 2 (Fut2)-dependent oligosaccharides and Lacto-N-Neotetraose (LNnT) present in the at least one nutritional composition B, and the amounts of Fucosyltransferase 2 (Fut2)-dependent oligosaccharides and Lacto-N-Neotetraose (LNnT) present in the at least one nutritional composition B exceed the amounts of Fucosyltransferase 2 (Fut2)-dependent oligosaccharides and Lacto-N-Neotetraose (LNnT) present in the at least one nutritional composition C. Preferably, also the amounts of Fucosyltransferase 2 (Fut2)-dependent oligosaccharides and Lacto-N-Neotetraose (LNnT) present in the at least one nutritional composition C are selected according to the age of the infants.

Typically, Fucosyltransferase 2 (Fut2)-dependent oligosaccharides are comprised in a nutritional composition C in an amount of from 0.8 to 2.2 g/L of composition, preferably from 1.0 to 2.0 g/L and more preferably from 1.4 to 1.8 g/L of composition. It is also preferred that Lacto-N-Neotetraose (LNnT) is comprised in a nutritional composition C in an amount of from 0.1 to 0.5 g/L of composition, preferably from 0.11 to 0.25 g/L and more preferably from 0.15 to 0.2 g/L of composition.

In a preferred embodiment, the present infant nutrition kit comprises a combination of the first nutritional composition A and the second nutritional composition B as defined above. Even more preferably, said kit further comprises the third nutritional composition C as defined above. Thus, the infant nutrition kit provides an age-tailored nutritional composition system for infants, which is specifically adapted to the evolving needs of these infants from between 0 and up to 4 months of age.

The kit may further comprise one or more of a fourth nutritional composition D for infants above 4 months of age, for instance for infants from 4 to 5, 6, 7, 8, 9, 10, 11, or 12 month of age, preferably in a quantity that is sufficient for feeding an infant from 4 month and up to 5, 6, 7, 8, 9, 10, 11, or 12 month of age.

Also said fourth nutritional composition D preferably comprises a combination of Fucosyltransferase 2 (Fut2)-dependent oligosaccharides and Lacto-N-Neotetraose (LNnT). Typically, nutritional compositions A, B, C and D differ from each other in the amount of Fucosyltransferase 2 (Fut2)-dependent oligosaccharides and Lacto-N-Neotetraose (LNnT) present therein, more typically such that the amounts of Fucosyltransferase 2 (Fut2)-dependent oligosaccharides and Lacto-N-Neotetraose (LNnT) present in the at least one nutritional composition A exceed the amounts of Fucosyltransferase 2 (Fut2)-dependent oligosaccharides and Lacto-N-Neotetraose (LNnT) present in the at least one nutritional composition B, the amounts of Fucosyltransferase 2 (Fut2)-dependent oligosaccharides and Lacto-N-Neotetraose (LNnT) present in the at least one nutritional composition B exceed the amounts of Fucosyltransferase 2 (Fut2)-dependent oligosaccharides and Lacto-N-Neotetraose (LNnT) present in the at least one nutritional composition C, and the amounts of Fucosyltransferase 2 (Fut2)-dependent oligosaccharides and Lacto-N-Neotetraose (LNnT) present in the at least one nutritional composition C exceed the amounts of Fucosyltransferase 2 (Fut2)-dependent oligosaccharides and Lacto-N-Neotetraose (LNnT) present in the at least one nutritional composition D. Preferably, also the amounts of Fucosyltransferase 2 (Fut2)-dependent oligosaccharides and Lacto-N-Neotetraose (LNnT) present in the at least one nutritional composition D are selected according to the age of the infants.

Typically, Fucosyltransferase 2 (Fut2)-dependent oligosaccharides are comprised in a nutritional composition D in an amount of less than 2.0 g/L of composition, preferably of less than 1.8 g/L of composition, more preferably of less than 1.4 g/L of composition, even more preferably of less than 1.0 g/L of composition and most preferably of less than 0.8 g/L of composition. It is also preferred that Lacto-N-Neotetraose (LNnT) is comprised in a nutritional composition D in an amount of less than 0.5 g/L of composition, preferably of less than 0.25 g/L of composition, more preferably of less than 0.2 g/L of composition, even more preferably of less than 0.15 g/L of composition and most preferably of less than 0.1 g/L of composition.

It is preferred that the Fucosyltransferase 2 (Fut2)-dependent oligosaccharides comprised in the nutritional compositions of the kit are selected from 2'Fucosyllactose (2'FL), di-Fucosyllactose (diFL), and Lacto-N-fucopentaose I (LNFP I), preferably from 2'Fucosyllactose (2'FL).

Optionally, the kit may comprise any further nutritional compositions E, F, etc. in a quantity that is sufficient for feeding an infant from four months of age up to 6, 7, 8, 9, 10, 11, or 12 months of age, and preferably from 5 up to 12 months, from 6 up to 11 months, from 7 up to 10 months, from 8 up to 9 months of age.

Typically, the individual nutritional compositions A, B, C, D, etc. of the kit are in the form of infant formulae, wherein these infant formulae can be either a complete or a partial substitute for human milk.

The nutritional compositions of the kit may be packed in single dose units, preferably wherein each single dose unit comprises a sufficient amount of nutritional composition to prepare a single serving upon reconstitution with water. The single dose units may be in the form of capsules, stick packs (blister packs) or sachets.

The individual nutritional compositions being part of the infant nutrition kit of the invention may be packed into individual single dose units and presented to the consumer in multipacks containing a sufficient number of single dose units to meet the requirements of an infant over a period of time, e.g. one week or one month.

For instance, the kit may comprise a certain quantity of single dose units comprising a sufficient amount of nutritional composition A, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition A.

Alternatively, or in addition, the kit may comprise a certain quantity of single dose units comprising a sufficient amount of nutritional composition B, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition B.

Alternatively, or in addition, the kit may also comprise a certain quantity of single dose units comprising a sufficient amount of nutritional composition C, e.g. from 1 to 60, from 2 to 50, from 3 to 40, from 4 to 30, from 5 to 20, from 6 to 15, from 7 to 12, or from 8 to 10 single dose units comprising a sufficient amount of nutritional composition C.

Alternatively, or in addition, the kit may also comprise a certain quantity of single dose units comprising a sufficient amount of nutritional composition D or E or F, etc. in the above-named amounts.

The present infant nutrition kit may be used in accordance with the nutritional composition of the invention.

Thus, the kit may be used in promoting any one of: head circumference growth rate in infants, brain growth and development in infants, brain catch-up growth in infants, cognitive function in infants, psychomotor development in infants, or any combination thereof.

Further, the present infant nutrition kit may be used in providing nutrition to an infant or for feeding an infant.

Preferably, the at least one nutritional composition A is used in infants between 0 up to 1 month of age, the at least one nutritional composition B is used in infants above 1 month and up to 2 months of age, the at least one nutritional composition C is used in infants above 2 months and up to 4 months of age, and the at least one nutritional composition D is used in infants above 4 months of age, for instance from 4 months of age up to 6, 7, 8, 9, 10, 11, or 12 months of age.

Use of the present infant nutrition kit is particularly advantageous in infants born from mothers with low Fut2 activity, who provide low levels of Fucosyltransferase 2 (Fut2)-dependent oligosaccharides and/or low levels of Lacto-N-Neotetraose LNnT in their breast milk.

Moreover, the present kit is adapted to the requirements for Fucosyltransferase 2 (Fut2)-dependent oligosaccharides and Lacto-N-Neotetraose of the developing infant, and, in particular, of infants who were born preterm or with low-birth weight or experienced intra-uterine growth retardation or suffered from growth stunting because of malnutrition and/or disease. For these infants, the present kit provides the "right concentration" of Fucosyltransferase 2 (Fut2)-dependent oligosaccharides and Lacto-N-Neotetraose "at the right time".

Advantageously, such adaption of the oligosaccharides dosage to the needs of infants of the given age avoids overdosing of oligosaccharides, thus reducing the risk of side effects associated with those ingredients such as gastrointestinal symptoms. Moreover, said adaptation of the oligosaccharides dosage over time enables an optimal supply with these compounds over the entire infant phase and thus stimulates brain growth and development in infants and particularly in preterm infants or extremely low gestational age newborns during their first year of life.

The present invention is further illustrated herein by means of the following non-limiting examples.

EXAMPLES

Example 1

Nutritional Composition Comprising Fut2-dependent Oligosaccharides and Lacto-N-Neotetraose A nutritional composition comprising Fucosyltransferase 2 (Fut2)-dependent oligosaccharides and Lacto-N-Neotetraose (LNnT) is given in Table 1 below:

TABLE 1

| | | |
|---|---|---|
| Basics | Reconstitution RTD Volume (ml) | 100 to 200 |
| | Energy density (kcal/100 ml) | 63-67 |
| | Content (g/100 kcal) | 1.8-2.25 |
| Protein | Content (g/l) | 11.3-15.1 |
| | Whey:Casein | 70:30 |
| | Type | Lactose |
| Carbohydrates | Content (g/100 kcal) | 9.7 to 11.6 |
| | Content (g/l) | 65.0 to 73.5 |
| Lipids | Type | Milk & Veg. |
| | Content (g/100 kcal) | 5.1 to 5.8 |
| | content (as % of total energy) | 45.9 to 52.2 |
| | Content (g/l) | 32.1 to 38.9 |
| | LC-PUFA | DHA + ARA |
| Probiotics | Type | B. lactis CNCM I-3446 and/or B. longum CNCM I-2618 |
| | Content | $2 \times 10^5$ cfu/g |
| HMOs (g/L) | 2'Fucosyllactose | 1 |
| | Lacto-N-neotetraose | 0.5 |
| Nucleotide | CMP (mg/100 kcal) | 1.1 |
| | UMP | 0.7 |
| | AMP | 0.7 |
| | GMP | 0.2 |
| Minerals (/100 kcal) | Na (mg) | 25 to 37.5 |
| | K (mg) | 80 to 95 |
| | Na/K (molar ratio) | 0.53-0.67 |
| | (Na + K)/Cl molar ratio | 1.71-1.81 |
| | Cl (mg) | 65 to 80 |
| | Ca (mg) | 60 |
| | P (mg) | 33 |
| | Mg (mg) | 7 |
| | Mn (μg) | 5 |
| | Ca/P | 1.8 |
| Vitamins (/100 kcal) | Vit. A (mg RE) | 0.09 to 01125 |
| | Vit. D (mg) | 0.0015 |
| | Vit. E (mg) | 1.3 |
| | Vit. K1 (μg) | 8 |
| | Vit. C (mg) | 15 |
| | Vit. B1 (mg) | 0.07 to 0.1 |
| | Vit. B2 (mg) | 0.1 |
| | Niacin (mg) | 0.5 |
| | Vit. B6 (mg) | 0.05 |
| | Folic acid (μg) | 15 to 16 |
| | Pantothenic Acid (mg) | 0.7 to 0.8 |
| | Vit. B12 (μg) | 0.2 |
| | Biotin (μg) | 2 |
| | Choline (mg) | 20 |
| | Inositol (mg) | 25 |
| | Taurine (mg) | 8 |
| | Carnitine (mg) | 1.5 |
| Trace Elements (/100 kcal) | Fe (mg) | 0.7 |
| | I (μg) | 15 to 20 |
| | Cu (mg) | 0.06 to 0.08 |
| | Zn (mg) | 1 to 1.2 |
| | Se (μg) | 3 to 4 |

\* fat mix follows AHA: sat. Fat <7% E + polyuns. <10% E LA/ALA 5.0
\*\* tfa

Example 2

Nutritional Compositions Comprising Fut2-dependent Oligosaccharides and Lacto-N-Neotetraose Age-tailored nutritional compositions comprising Fucosyltransferase 2 (Fut2)-dependent oligosaccharides and Lacto-N-Neotetraose (LNnT) are given in Table 2 below:

TABLE 2

| | | Composition | | | |
|---|---|---|---|---|---|
| | | A | B | C | D |
| | | Age range | | | |
| | | 0 up to 1 month | 1 up to 2 months | 2 up to 4 months | Above 4 months |
| Basics | Reconstitution RTD Volume (ml) | 100 to 200 | 100 to 200 | 100 to 200 | 100 to 200 |
| | Energy density (kcal/100 ml) | 63-67 | 63-67 | 63-67 | 63-67 |

TABLE 2-continued

|  |  | Composition A | Composition B | Composition C | Composition D |
|---|---|---|---|---|---|
|  |  | Age range | | | |
|  |  | 0 up to 1 month | 1 up to 2 months | 2 up to 4 months | Above 4 months |
| Protein | Content (g/100 kcal) | 1.8-2.25 | 1.8-2.25 | 1.8-2.25 | 1.8-2.25 |
|  | Content (g/l) | 11.3-15.1 | 11.3-15.1 | 11.3-15.1 | 11.3-15.1 |
|  | Whey:Casein | 70:30 | 70:30 | 70:30 | 70:30 |
| Carbohydrates | Type | Lactose | Lactose | Lactose | Lactose |
|  | Content (g/100 kcal) | 9.7 to 11.6 | 9.7 to 11.6 | 9.7 to 11.6 | 9.7 to 11.6 |
|  | Content (g/l) | 65.0 to 73.5 | 65.0 to 73.5 | 65.0 to 73.5 | 65.0 to 73.5 |
| Lipids | Type | Milk & Veg. | Milk & Veg. | Milk & Veg. | Milk & Veg. |
|  | Content (g/100 kcal) | 5.1 to 5.8 | 5.1 to 5.8 | 5.1 to 5.8 | 5.1 to 5.8 |
|  | content (as % of total energy) | 45.9 to 52.2 | 45.9 to 52.2 | 45.9 to 52.2 | 45.9 to 52.2 |
|  | Content (g/l) | 32.1 to 38.9 | 32.1 to 38.9 | 32.1 to 38.9 | 32.1 to 38.9 |
|  | LC-PUFA | DHA + ARA | DHA + ARA | DHA + ARA | DHA + ARA |
| Probiotics | Type | B. lactis CNCM I-3446 and/or B. longum CNCM I-2618 | B. lactis CNCM I-3446 and/or B. longum CNCM I-2618 | B. lactis CNCM I-3446 and/or B. longum CNCM I-2618 | B. lactis CNCM I-3446 and/or B. longum CNCM I-2618 |
|  | Content | $2 \times 10^5$ cfu/g | $2 \times 10^5$ cfu/g | $2 \times 10^5$ cfu/g | $2 \times 10^5$ cfu/g |
| HMOs (g/L) | 2'Fucosyllactose | 3 | 2.2 | 1.8 | 1.4 |
|  | Lacto-N-neotetraose | 0.5 | 0.3 | 0.2 | 0.15 |
| Nucleotide | CMP (mg/100 kcal) | 1.1 | 1.1 | 1.1 | 1.1 |
|  | UMP | 0.7 | 0.7 | 0.7 | 0.7 |
|  | AMP | 0.7 | 0.7 | 0.7 | 0.7 |
|  | GMP | 0.2 | 0.2 | 0.2 | 0.2 |
| Minerals (/100 kcal) | Na (mg) | 25 to 37.5 | 25 to 37.5 | 25 to 37.5 | 25 to 37.5 |
|  | K (mg) | 80 to 95 | 80 to 95 | 80 to 95 | 80 to 95 |
|  | Na/K (molar ratio) | 0.53-0.67 | 0.53-0.67 | 0.53-0.67 | 0.53-0.67 |
|  | (Na + K)/Cl molar ratio | 1.71-1.81 | 1.71-1.81 | 1.71-1.81 | 1.71-1.81 |
|  | Cl (mg) | 65 to 80 | 65 to 80 | 65 to 80 | 65 to 80 |
|  | Ca (mg) | 60 | 60 | 60 | 60 |
|  | P (mg) | 33 | 33 | 33 | 33 |
|  | Mg (mg) | 7 | 7 | 7 | 7 |
|  | Mn (µg) | 5 | 5 | 5 | 5 |
|  | Ca/P | 1.8 | 1.8 | 1.8 | 1.8 |
| Vitamins (/100 kcal) | Vit. A (mg RE) | 0.09 to 01125 | 0.09 to 01125 | 0.09 to 01125 | 0.09 to 01125 |
|  | Vit. D (mg) | 0.0015 | 0.0015 | 0.0015 | 0.0015 |
|  | Vit. E (mg) | 1.3 | 1.3 | 1.3 | 1.3 |
|  | Vit. K1 (µg) | 8 | 8 | 8 | 8 |
|  | Vit. C (mg) | 15 | 15 | 15 | 15 |
|  | Vit. B1 (mg) | 0.07 to 0.1 | 0.07 to 0.1 | 0.07 to 0.1 | 0.07 to 0.1 |
|  | Vit. B2 (mg) | 0.1 | 0.1 | 0.1 | 0.1 |
|  | Niacin (mg) | 0.5 | 0.5 | 0.5 | 0.5 |
|  | Vit. B6 (mg) | 0.05 | 0.05 | 0.05 | 0.05 |
|  | Folic acid (µg) | 15 to 16 | 15 to 16 | 15 to 16 | 15 to 16 |
|  | Pantothenic Acid (mg) | 0.7 to 0.8 | 0.7 to 0.8 | 0.7 to 0.8 | 0.7 to 0.8 |
|  | Vit. B12 (µg) | 0.2 | 0.2 | 0.2 | 0.2 |
|  | Biotin (µg) | 2 | 2 | 2 | 2 |
|  | Choline (mg) | 20 | 20 | 20 | 20 |
|  | Inositol (mg) | 25 | 25 | 25 | 25 |
|  | Taurine (mg) | 8 | 8 | 8 | 8 |
|  | Carnitine (mg) | 1.5 | 1.5 | 1.5 | 1.5 |
| Trace Elements (/100 kcal) | Fe (mg) | 0.7 | 0.7 | 0.7 | 0.7 |
|  | I (µg) | 15 to 20 | 15 to 20 | 15 to 20 | 15 to 20 |
|  | Cu (mg) | 0.06 to 0.08 | 0.06 to 0.08 | 0.06 to 0.08 | 0.06 to 0.08 |
|  | Zn (mg) | 1 to 1.2 | 1 to 1.2 | 1 to 1.2 | 1 to 1.2 |
|  | Se (µg) | 3 to 4 | 3 to 4 | 3 to 4 | 3 to 4 |

\* fat mix follows AHA: sat. Fat <7% E + polyuns. <10% E LA/ALA 5.0
\*\* tfa
\*\*\* Nutritional composition A is for use in infants between 0 and 1 months of age, nutritional composition B is for use in infants between 0 and 2 months of age, nutritional composition C is for use in infants between 0 and 4 months of age, and nutritional composition D is for use in infants older than 4 months of age and up to 12 months of age.

Example 3

Nutritional Composition Kit

The kit comprises each one of nutritional compositions A, B, C and D as described in Example 2 in the form of an infant formula packed in a single dose unit, e.g. a sachet, stick pack, blister pack or capsule.

Example 4

Clinical Trial on Normal Ranges of Fut2-dependent Oligosaccharides and Lacto-N-Neotetraose in Breast Milk of Healthy Mothers with Low and High Fut2 Activity Study Design An open, single-centre, 1 group study was conducted including 50 subjects (mothers) lasting 4 months. Only healthy volunteers were included.

All subjects complied with all the following inclusion criteria: 1. Gestational age between 37 and not above 42 weeks, 2. Baby to be enrolled between birth and V1, 3. Mother not younger than 18 years and not older than 40 years of age, 4. pre-pregnancy BMI of the mother between 18.5-29.5. Mothers willing to breastfeed for the first 4 months after giving birth.

Subjects representing one or more of the following criteria are excluded from participation in the study: 1. Gestational diabetes, 2. HTA>140/90, 3. Mothers who are smokers while breast-feeding, 4. Subject who cannot be expected to comply with the study procedures. 5. Currently participating or having participated in another clinical trial during the last 12 weeks prior to the beginning of this study.

Oligosaccharides Sample Preparation and Analysis

Analysis of oligosaccharides (2'Fucosyllactose and Lacto-N-Neotetraose) was conducted in duplicates on a 10 mL sample of whole breast milk fully expressed mature milk, corresponding to a complete feed, and taken after 30, 60 and 120 days after infants' birth (post partum).

Oligosaccharide analysis was done in duplicates as follows.

Sample Preparation

Briefly, 1 mL of well mixed whole breast milk was centrifuged for 20 min at 1700×g. About 0.1 mL of skimmed milk supernatant was diluted 10× with water and 0.01 mL of the thus diluted supernatant were taken as a sample for analysis.

Analysis

Samples were analyzed by high performance ion exchange chromatography (HPAEC; Thermo, Dionex, Ca) equipped with a CarboPac PA1 column (Thermo, Dionex, Ca) for separation and a pulsed amperometric detector (PAD) for detection of carbohydrates. Oligosaccharide identification was done based on comparison of retention times to authentic standards and enzymatic hydrolysis of samples (e.g. fucosidase, galactosidase). Oligosaccharide quantification was done using external standard curves with pure authentic oligosaccharides.

Statistical Methods

Data collection points were 30, 60 and 120 days after infants' birth. Means with standard deviation were calculated for 2'Fucosyllactose (2'FL) and Lacto-N-neotetraose levels measured in breast milk grouped into samples with (i) low Fut2 activity (≤0.2 g/L 2'FL) and (ii) high Fut2 activity (>0.2 g/L 2'FL). Statistical difference of 2'FL and LNnT levels between the two groups was assessed by t-test.

Results

Figure 1B:
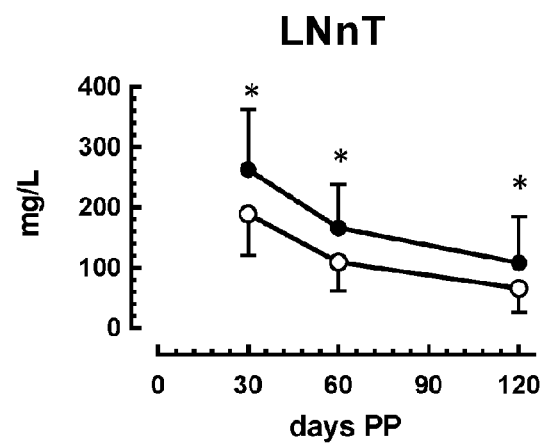
FIG. 1b depicts Lacto-N-neotetraose (LNnT) levels in milk with high (closed circles) and low (open circles) Fucosyltransferase 2 (Fut2)-dependent milk oligosaccharides (OS) at 30, 60 and 120 days post partum (PP). * Indicate significant difference by t-test at specific day PP.

The results of the study are shown in FIGS. 1A and 1B. The corresponding data is summarized in Table 3.

As can be seen from FIG. 1A the concentration of Fut2-dependent oligosaccharides in human breast milk from mothers showing high Fut2 activity, as seen in 2'Fucosyllactose levels above 0.2 g/L in milk, decreases with time from about 2.2 g/L to about 1.8 g/L to about 1.4 g/L, as determined at day 30, 60 and 120 after infants' birth. Milk samples with very low detected 2'FL of less than 0.2 g/L were grouped in the low Fut2 activity group. These samples showed mean levels of 2'FL decreasing from about 0.03 g/L to about 0.01 g/L, as determined at day 30, 60 and 120 after infants' birth.

As can be seen from FIG. 1B the concentration of Lacto-N-Neotetraose in human breast milk from both, mothers with high and low Fut2 activity, decreases with time as determined after 30, 60 and 120 days after infants' birth. Moreover, it can be seen that the concentrations of Lacto-N-Neotetraose in human breast milk from mothers with high Fut2 activity are significantly higher at each time point, i.e. at 30, 60 and 120 days post partum, as compared to the concentrations of Lacto-N-Neotetraose in human breast milk from mothers with low Fut2 activity.

Conclusion

These results suggest a correlation between low Fut2 activity, low Fut2-dependent oligosaccharide levels and low levels of Lacto-N-neotetraose in human breast milk. The data also demonstrates that high Fut2 activity not only leads to increased Fut2-dependent oligosaccharide levels in breast milk, but also to increased Lacto-N-neotetraose levels as compared to the respective levels in breast milk from mothers with low Fut2 activity.

Example 5

Clinical Trial on the Head Circumference Rate of Infants Receiving Breast Milk from Healthy Mothers with Low and High Fut2 Activity Head circumference (HC) growth rates were determined in infants receiving breast milk from healthy mothers with low Fut2 activity (≤0.2 g/L 2'FL) and high FUT2 activity (>0.2 g/L 2'FL) at 30, 60 and 120 days after infants' birth.

The study was performed as described in Example 4. Further, HC was measured using a measuring tape at a specific position of the infant's head where the head has the largest circumference, just above the eyebrows and ears, and around the back of the head where it slopes up prominently from the neck.

Data collection points were 30, 60 and 120 days after infants' birth. Head circumference (HC) growth rates were calculated for each infant as follows:

[(HC at time point 30, 60 or 120 days after birth)−(HC at birth)]/number of days after birth (30, 60 or 120)

Means with standard deviation of HC growth rate were calculated and ANOVA was used to assess statistical significance of HC growth rates at each time point between the group with low and high FUT2 activity.

Results

Figure 2:
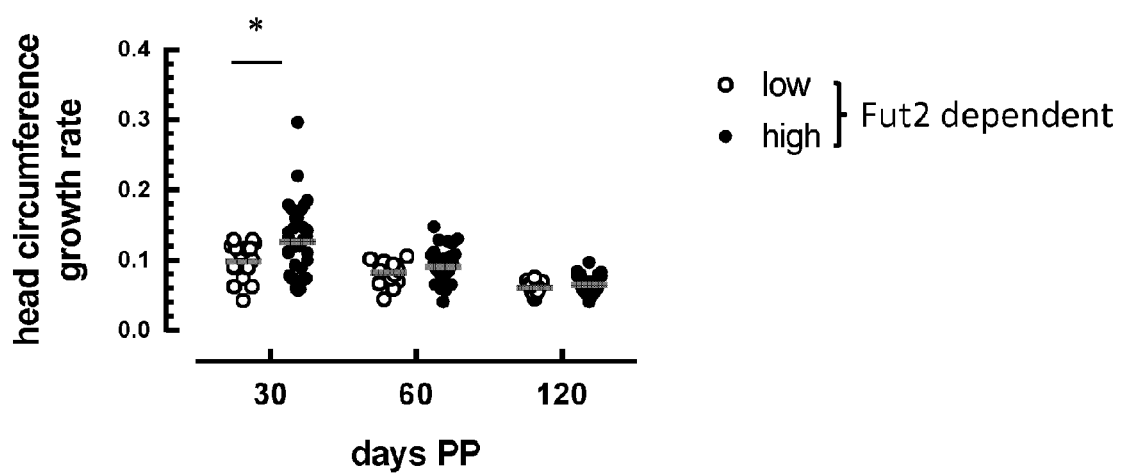
FIG. 2 depicts head circumference growth rate of infants at 30, 60 and 120 days post partum (PP) who consumed mother milk with low (open circles) or high (closed circles) Fucosyltransferase 2 (Fut2)-dependent milk oligosaccharides (OS). Grey bar indicates mean values and * indicates statistical significance by ANOVA.

The results of the study are shown in FIG. 2.

Infants receiving breast milk from mothers showing high Fut2 activity (as seen in 2'Fucosyllactose levels above 0.2 g/L in milk) displayed a higher head circumference growth rate at 30 days of age as compared to infants who consumed breast milk from mothers showing low Fut2 activity as seen in 2'Fucosyllactose levels of 0.2 g/L in milk, or lower. At 60 and 120 days of age the head circumference growth rate was almost equal between the high Fut2 activity group (>0.2 g/L 2'FL) and the low FUT2 activity group 0.2 g/L 2'FL).

The data obtained from Examples 3 and 4 is summarized in Table 3 below.

TABLE 3

| | days post partum | low FUT2 activity | | high FUT2 activity | | |
|---|---|---|---|---|---|---|
| | | mean | STD | mean | STD | p |
| 2'FL | 30 | 0.03 | 0.03 | 2.2 | 0.8 | n/a |
| (g/L) | 60 | 0.02 | 0.01 | 1.8 | 0.6 | n/a |
| | 120 | 0.01 | 0.005 | 1.4 | 0.6 | n/a |
| LNnT | 30 | 0.19 | 0.07 | 0.26 | 0.1 | 0.01 |
| (g/L) | 60 | 0.11 | 0.05 | 0.17 | 0.07 | 0.006 |
| | 120 | 0.07 | 0.04 | 0.11 | 0.08 | 0.04 |
| HC gr | 30 | 0.098 | 0.026 | 0.127 | 0.05 | <0.01 |
| | 60 | 0.082 | 0.016 | 0.089 | 0.024 | ns |
| | 120 | 0.061 | 0.009 | 0.065 | 0.013 | ns | ns, not significant
n/a, not applicable

Table 3 shows mean levels with standard deviation (STD) of 2'Fucosyllactose (2'FL) and Lacto-N-neotetraose (LNnT) in breast milk grouped by low (2'FL<0.2 g/L) and high (2'FL>0.2 g/L) Fut2 activity over the first 120 days post partum compared to head circumference growth rate (HC gr) at the same time points in infants who consumed such milk (n=50). Statistical testing was performed by t-test for LNnT and by ANOVA for HC gr.

Conclusion

Head circumference growth rate is a proposed proxy for brain catch-up growth and development. Thus, these results suggest that a high Fut2 activity, and, thus, increased levels of Fut2-dependent oligosaccharides and Lacto-N-neotetraose in breast milk have a particularly high impact on brain catch-up growth and brain development in infants, in particular in the very early post-natal period.

Example 6

Clinical Trial on Normal Ranges of 6'Sialyllactose (6'SL) and 3'Sialyllactose (3'SL) in Breast Milk of Healthy Mothers with Low and High Fut2 Activity 6'Sialyllactose (6'SL) and 3'Sialyllactose (3'SL) levels were determined in the breast milk from healthy mothers with low Fut2 activity (≤0.2 g/L 2'FL) and high FUT2 activity (>0.2 g/L 2'FL) at 30, 60 and 120 days after infants' birth.

The study was performed as described in Example 4.

In particular, analysis of 6'Sialyllactose (6'SL) and 3'Sialyllactose (3'SL) was conducted in duplicates on a 10 mL sample of whole breast milk fully expressed mature milk, corresponding to a complete feed, and taken after 30, 60 and 120 days after infants' birth (post partum).

Means with standard deviation were calculated for 6'Sialyllactose (6'SL) and 3'Sialyllactose (3'SL) levels measured in breast milk grouped into samples with (i) low Fut2 activity (≤0.2 g/L 2'FL) and (ii) high Fut2 activity (>0.2 g/L 2'FL). Statistical difference of 2'FL and LNnT levels between the two groups was assessed by t-test.

Results

Figure 3A:
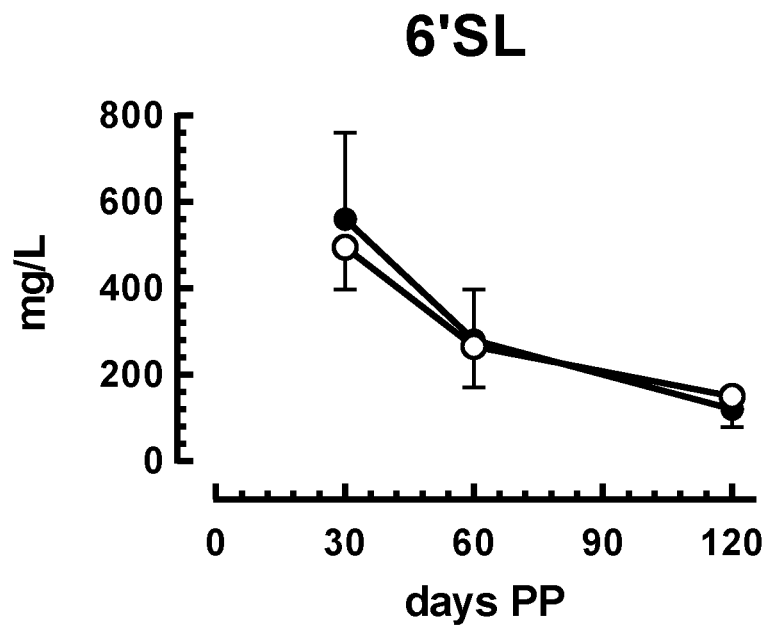
FIG. 3a depicts 6'Sialyllactose (6'SL) levels in milk with high (closed circles) and low (open circles) Fucosyltransferase 2 (Fut2)-dependent milk OS at 30, 60 and 120 days post partum (PP). * Indicate significant difference by t-test at specific day PP.
Figure 3B:
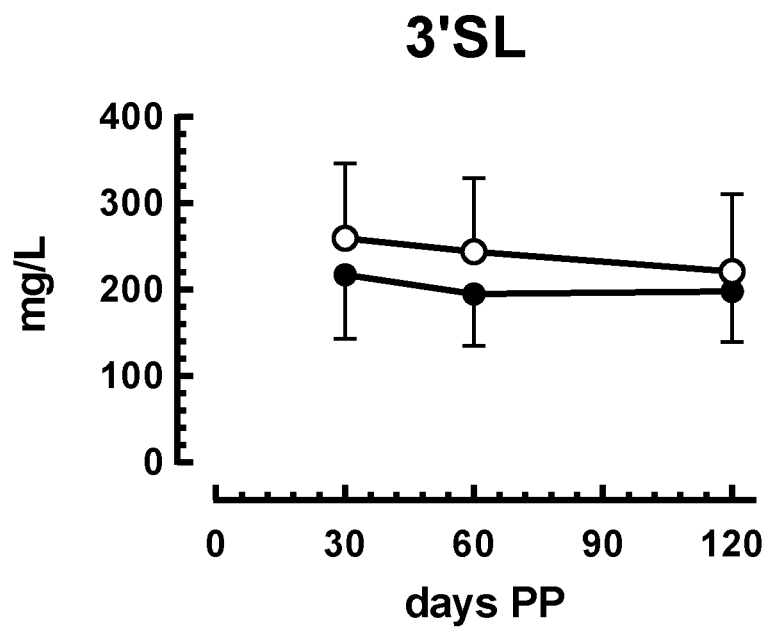
FIG. 3b depicts 3'Sialyllactose (3'SL) levels in milk with high (closed circles) and low (open circles) Fucosyltransferase 2 (Fut2)-dependent milk OS at 30, 60 and 120 days post partum (PP). * Indicate significant difference by t-test at specific day PP.

The results of the study are shown in FIGS. 3A and 3B. As can be seen from these Figures, no significant differences in the 6'Sialyllactose (6'SL) and 3'Sialyllactose (3'SL) levels were found between the high Fut2 activity (>0.2 g/L 2'FL) group and the low Fut2 activity (≤0.2 g/L 2'FL) group at day 30, 60 and 120 after infants' birth.

The concentrations of 6'Sialyllactose (6'SL) and 3'Sialyllactose (3'SL) in human breast milk from both, mothers with high and low Fut2 activity equally decreases with time as determined after 30, 60 and 120 days after infants' birth.

Conclusion

These results suggest that there is no correlation between high Fut2 activity or high Fut2-dependent oligosaccharide levels, respectively, and the concentration of other human milk oligosaccharides such as 6'Sialyllactose (6'SL) and 3'Sialyllactose (3'SL) in human breast milk.

Having thus described the present invention in detail and the advantages thereof, it is to be understood that the detailed description is not intended to limit the scope of the invention thereof.

The invention claimed is:

1. A method for promoting brain growth and development in an infant between 0 and 4 months of age in need of brain catch-up growth, the method comprising administering a nutritional composition comprising 2'Fucosyllactose (2'FL) and Lacto-N-Neotetraose (LNnT) to the infant, the nutritional composition does not contain probiotics, and the amount of 2'-fucosyllactose is between 0.8-8.0 g/L of the nutritional composition.

2. The method according to claim 1, wherein the infant is between 0 and 2 months of age.

3. The method according to claim 1, wherein the nutritional composition is administered to the infant in an amount effective for achieving a characteristic selected from the group consisting of: head circumference growth rate in infants, brain catch-up growth in infants, cognitive function in infants, psychomotor development in infants, and any combination thereof.

4. The method according to claim 1, wherein the nutritional composition provides nutrition to the infant.

5. The method according to claim 1, wherein the nutritional composition is administered to the infant in addition to breast feeding.

6. The method according to claim 1, wherein the Lacto-N-Neotetraose (LNnT) is 0.1 to 0.6 g/L of the nutritional composition.

7. The method according to claim 1, wherein the nutritional composition further comprises at least one additional Fucosyltransferase 2 (Fut2)-dependent oligosaccharide selected from the group consisting of di-Fucosyllactose (diFL) and Lacto-N-fucopentaose I (LNFP I).

8. The method according to claim 1, wherein the nutritional composition is in a form selected from the group consisting of an infant formula, a preterm infant formula, a human milk fortifier, a starter infant formula, a follow-on formula, a baby food formula, a medical food product for clinical nutrition and a supplement.

9. The method according to claim 1, wherein the infant was born preterm or with low-birth weight or experienced intra-uterine growth retardation or suffered from growth stunting because of malnutrition and/or a disease.

10. The method according to claim 1, wherein the infant was born from a mother with low Fut2 activity with a 2'Fucosyllactose concentration in breast milk of the mother of less than 0.2 g/L.

11. A method to provide nutrition to an infant between 0 and 4 months of age in need of brain catch-up growth, the method comprising feeding a nutritional composition comprising 2'Fucosyllactose (2'FL) and Lacto-N-Neotetraose (LNnT) to the infant, the nutritional composition does not contain probiotics, and the amount of 2'-fucosyllactose is between 0.8-8.0 g/L of the nutritional composition.

12. The method according to claim 1, wherein the infant is between birth and 1 month of age, the Lacto-N-Neotetraose (LNnT) is 0.30 to 0.35 g/L of composition, and the 2'Fucosyllactose (2'FL) is 2.0 to 2.2 g/L of the nutritional composition.

13. The method according to claim 1, further comprising adding the nutritional composition to breast milk from the mother of the infant prior to the administering.

\* \* \* \* \*